(12) United States Patent
Sleevi et al.

(10) Patent No.: US 10,947,521 B2
(45) Date of Patent: Mar. 16, 2021

(54) PROCESS FOR PRODUCING RECOMBINANT TRYPSIN

(71) Applicant: Merck Sharp & Dohme Corp., Rahway, NJ (US)

(72) Inventors: Mark C. Sleevi, Longmont, CO (US); Jack Lile, Aurora, CO (US)

(73) Assignee: MERCK SHARP & DOHME CORP., Rahway, NJ (US)

(*) Notice: Subject to any disclaimer, the term of this patent is extended or adjusted under 35 U.S.C. 154(b) by 168 days.

(21) Appl. No.: 15/526,772

(22) PCT Filed: Nov. 13, 2015

(86) PCT No.: PCT/US2015/060505
§ 371 (c)(1),
(2) Date: May 15, 2017

(87) PCT Pub. No.: WO2016/081289
PCT Pub. Date: May 26, 2016

(65) Prior Publication Data
US 2017/0335308 A1    Nov. 23, 2017

Related U.S. Application Data

(60) Provisional application No. 62/081,258, filed on Nov. 18, 2014.

(51) Int. Cl.
| | | |
|---|---|---|
| C12N 9/76 | (2006.01) | |
| G06N 3/08 | (2006.01) | |
| G06N 3/04 | (2006.01) | |
| G06F 40/216 | (2020.01) | |
| G06F 40/253 | (2020.01) | |
| G06F 40/289 | (2020.01) | |

(52) U.S. Cl.
CPC .... *C12N 9/6427* (2013.01); *C12Y 304/21004* (2013.01); *G06F 40/216* (2020.01); *G06F 40/253* (2020.01); *G06F 40/289* (2020.01); *G06N 3/0454* (2013.01); *G06N 3/088* (2013.01)

(58) Field of Classification Search
CPC .................................................. C12N 9/6427
See application file for complete search history.

(56) References Cited

U.S. PATENT DOCUMENTS

| | | | | |
|---|---|---|---|---|
| 7,893,210 B2* | 2/2011 | Peters | ............... | C07K 1/1133 530/351 |
| 2005/0014933 A1* | 1/2005 | Peters | ............... | C07K 1/1133 530/351 |
| 2012/0135460 A1 | 5/2012 | Pridmore et al. | | |

FOREIGN PATENT DOCUMENTS

| | | |
|---|---|---|
| WO | 9311240 | 6/1993 |
| WO | 200119970 | 3/2001 |
| WO | 2008008975 | 1/2008 |
| WO | 2012104099 | 8/2012 |

OTHER PUBLICATIONS

P00761. UniProtKB Database. 2013.*
Honda. Large-Scale Refolding of Therapeutic Proteins. Bioseparation Engineering. pp. 101-105. 2000.*
Craik et al., J. Biol. Chem. vol. 259, 1984, pp. 14255-14262.
Fletcher et al., Biochemistry, Vo. 26, 1987, pp. 3081-3086.
Vasquez et al., J. Cell Biochem., vol. 39, 1989, pp. 265-276.
Kay and Kassell, J. Biol. Chem. vol. 246, 1971, pp. 6661-6665.
Grant and Hermon-Taylor, Biochem. J., vol. 147, 1975, pp. 363-366.
Hohenblum et al., J. Biotechnol. vol. 109, 2004, pp. 3-11.
Brodrick et al., J. Biol. Chem. vol. 253, 1978, pp. 2732-2736.
Kukor et al., Eur. J. Biochem., vol. 270, 2003, pp. 2047-2058.
Vallejo, L. F. et al., Strategies for the recovery of active proteins through refolding of bacterial inclusion body proteins. Microbial. Cell Factories, vol. 3, No. 1, 2004, p. 11.
Ohshima et al., Refolding of Fully Reduced Bovine Pancreatic and Bioengineering, Elsevier, Amsterdam, NL, vol. 106, No. 4, 2008, pp. 345-349.
Wang et al., Purification cDNA cloning and recombinant expression of chymotrypsin C from porcine pancreas, Acta Biochimica et Biophysica Sinica, 2011, No. 7, pp. 568-575, 43.

* cited by examiner

*Primary Examiner* — Yong D Pak
(74) *Attorney, Agent, or Firm* — David Van Goor; Anna L. Cocuzzo

(57) ABSTRACT

A process for producing recombinant trypsin from prokaryote host cells in high yield and high specific activity is described. In particular, a process for producing recombinant trypsin from *E. coli* is described.

21 Claims, 1 Drawing Sheet

Specification includes a Sequence Listing.

MFPTDDDDKI VGGYTCAANS IPYQVSLNSG SHFCGGSLIN SQWVVSAAHC
YKSRIQVRLG EHNIDVLEGN EQFINAAKII THPNFNGNTL DNDIMLIKLS
SPATLNSRVA TVSLPRSCAA AGTECLISGW GNTKSSGSSY PSLLQCLKAP
VLSDSSCKSS YPGQITGNMI CVGFLEGGKD SCQGDSGGPV VCNGQLQGIV
SWGYGCAQKN KPGVYTKVCN YVNWIQQTIA AN

PROCESS FOR PRODUCING RECOMBINANT TRYPSIN

CROSS REFERENCE TO RELATED APPLICATIONS

This application is the National Stage of International Application No. PCT/US2015/060505 filed on Nov. 13, 2015, which claims benefit of U.S. Provisional Application No. 62/081,258 filed Nov. 18, 2014, each of which is incorporated herein by reference in its entirety.

BACKGROUND OF THE INVENTION

(1) Field of the Invention

The present invention provides a process for producing recombinant trypsin from prokaryote host cells in high yield and high specific activity. In particular, the present invention provides a process for producing recombinant trypsin from *E. coli*.

(2) Description of Related Art

Trypsin is a serine protease widely used in commercial processes for making various therapeutic proteins. Trypsin cleaves the peptide bond on the carboxy-terminus of basic amino acid residues such as lysine and arginine. In animals, trypsin plays a pivotal role among pancreatic enzymes in the activation of endopeptidases. These pancreatic enzymes are secreted through the pancreatic duct into the duodenum of the small intestine in response to a hormone signal generated when food passes from the stomach. They are not, however, synthesized in their final active form. Rather, they are made as slightly longer catalytically inactive molecules called zymogens. The names given to some of these zymogens include trypsinogen, chymotrypsinogen, proelastase, and procarboxypeptidase. These zymogens must themselves be cleaved proteolytically to yield active enzymes.

The first step of the activation cascade is the activation of trypsin from trypsinogen in the duodenum. Enteropeptidase (also known as enterokinase) is a protease produced by duodenal epithelial cells which activates pancreatic trypsinogen to trypsin by excising an octapeptide leader sequence from the amino-terminus of trypsinogen. Trypsin in turn autocatalytically activates more trypsinogen to trypsin and also acts on other proenzymes, thus, for example, liberating the endopeptidases chymotrypsin and elastase as well as carboxypeptidases A and B. To activate trypsin from its inactive precursor, a leader sequence on the amino-terminus of trypsinogen is enzymatically removed. Trypsinogens of many different species have been cloned and characterized.

Trypsins have a variety of uses. They are useful for the characterization of other proteins as well as in the manufacturing process of other recombinant biological products. For example, small recombinant proteins are often expressed first as fusion proteins to facilitate their purification and enhance their stability. The fusion proteins can be engineered such that a leader sequence can be cleaved from the native protein sequence by trypsin. Any internal lysine residues or arginine residues that are not part of the leader sequence can be chemically protected from cleavage by trypsin. Trypsin and chymotrypsin have been used for the manufacture of insulin and insulin analogs and for the manufacture of various vaccine products.

Trypsinogens from various species have been isolated and characterized (Craik et al., J. Biol. Chem. 259: 14255-14264 (1984); Fletcher et al., Biochemistry 26: 3081-3086 (1987)). However, bovine trypsin, isolated from bovine pancreas, or porcine trypsin, isolated from porcine pancreas, are now largely used in research laboratories and are the trypsins of choice for protein processing in the pharmaceutical industry. Even after extensive purification of animal-derived trypsin, however, there are contaminating activities in most preparations that can have undesirable consequences for both experimental research and pharmaceutical therapeutic protein processing. For example, the emergence of diseases such as transmissible spongiform encephalopathy (TSE) has raised concerns about the use of enzymes from animal original in industrial processes.

In addition, strict guidelines and regulations issued by the Food and Drug Administration as well as other national and international regulatory bodies have led to a need for pure trypsin of recombinant origin. The present invention addresses this need by providing recombinantly expressed trypsinogens which can be purified in large quantities. These trypsinogens can be produced stably in a variety of expression systems and subsequently activated to provide pure trypsin for use in both experimental research and industrial therapeutic protein processing.

Heretofore, the efficient manufacture of large quantities of recombinant trypsin useful in the manufacture of protein pharmaceuticals has been problematic. Problems have stemmed from such factors as the instability of mature trypsin in expression systems, the activation of trypsinogen during expression by endogenous host cell enzymes and subsequent damage to cell membranes, the low solubility of expressed protein in bacterial host cell systems, and improper folding of the protein in various host cell systems. Moreover, presently available commercial preparations of animal-derived trypsin all suffer from the presence of contaminating chymotryptic activity, which either necessitates the addition of inhibitors or results in illegitimate cleavage products.

One type of bacterial expression system has been developed for rat anionic trypsin (Vasquez et al., J. Cell. Biochem. 39: 265276 (1989)). In this system the rat trypsin leader sequence is replaced with the phoA signal peptide which directs the secretion of trypsin to the periplasmic space of *E. coli*. The signal peptide is removed from the fusion protein during secretion into the periplasmic space.

Trypsin contains three internal trypsin cleavage sites in addition to the cleavage site in the leader sequence, and trypsin has a strong affinity for itself. These features account for the consistent failure of others to develop an effective recombinant expression system. Because of these internal cleavages sites and this high self-affinity, the recombinant trypsinogen becomes activated to mature trypsin during expression and/or secretion. These activated trypsin molecules then cleave other recombinantly produced trypsin enzymes at internal cleavage sites and render these enzymes inactive. The resulting mixture of recombinant trypsin peptides thus contains only a small percentage of intact active trypsin. This self-cleavage contributes to low yields of recombinant trypsinogen or trypsin.

Thus, there exists a need in the art for an efficient and inexpensive means to produce recombinant trypsin which can then be used to safely and consistently manufacture other protein therapeutics, without unwanted cleavage products. Accordingly, the present invention provides an efficient and relatively inexpensive process to manufacture recombinant trypsin.

BRIEF SUMMARY OF THE INVENTION

The present invention provides a process for making recombinant trypsin from its zymogen trypsinogen produced from a prokaryote host cell at high yield. The process allows for refolding to take place at much higher protein concentrations than has been previously reported and in the presence of a low molecular weight reducing agent without a low molecular weight oxidizing agent, i.e., without a low molecular weight redox pair. The process results in much higher refold efficiencies than have been previously attainable for trypsin produced from a prokaryote host cell. The ability to achieve high refold efficiencies enables the production of a recombinant trypsin at commercially relevant amounts.

Therefore, the present invention provides a process for refolding recombinant trypsinogen produced from a prokaryote host cell comprising (a) providing the recombinant trypsinogen in a solubilization solution comprising a chaotropic agent, a buffer agent, and a low molecular weight reducing agent in the absence of a low molecular weight oxidizing agent; and (b) infusing the solubilization solution comprising the recombinant trypsinogen over time into a diluent comprising the chaotropic agent, buffer agent, and low molecular weight reducing agent in the absence of a low molecular weight oxidizing agent to provide a refold solution comprising the recombinant trypsinogen at a concentration greater than 1 g/L or from about 1.5 to 1.9 g/L or about 1.8 g/L and incubating the refold solution comprising the recombinant trypsinogen for a time sufficient for the recombinant trypsinogen to refold into a conformation characteristic of native trypsinogen and form the disulfide bonds characteristic of native trypsinogen. In particular aspects, the prokaryote host cell is $E.\ coli$.

In particular embodiments of the process, the chaotropic agent in the solubilization solution is about 5 to 10 M or about 6.45 M. In particular aspects, the chaotropic agent in the refold solution is about 1.4 to 1.8 M. In particular aspects of the present invention, the chaotropic agent in the solubilization solution and the refold solution is urea.

In particular embodiments of the process, the solubilization solution comprises 10 to 20 g/L of trypsinogen and the low molecular weight reducing agent in the solubilization solution comprising the recombinant trypsinogen is at a concentration sufficient to provide about 1 to 15 or about 5 to 10 SH residues of the low molecular weight reducing agent per cysteine residue of the recombinant trypsinogen. In particular embodiments of the process, solubilization solution comprises about 16 g/L of trypsinogen and the low molecular weight reducing agent in the solubilization solution comprising the recombinant trypsinogen is at a concentration sufficient to provide about 5.7 SH residues of the low molecular weight reducing agent per cysteine residue of the recombinant trypsinogen.

In particular aspects of the process, the low molecular weight reducing agent in the refold solution comprising the recombinant trypsinogen is at a concentration sufficient to provide about 1 to 30 SH residues of the low molecular weight reducing agent per cysteine residue of the recombinant trypsinogen. In particular aspects of the process, the low molecular weight reducing agent in the refold solution comprising the recombinant trypsinogen is at a concentration sufficient to provide about 2 to about 25 SH residues of the low molecular weight reducing agent per cysteine residue of the recombinant trypsinogen. In particular aspects, the low molecular weight reducing agent in the refold solution comprising the recombinant trypsinogen is at a concentration sufficient to provide about 11 to about 23 SH residues of the low molecular weight reducing agent per cysteine residue of the recombinant trypsinogen. In particular aspects, the low molecular weight reducing agent is cysteine or cysteine hydrochloride or L-cysteine or L-cysteine hydrochloride. In particular aspects, the low molecular weight reducing agent is dithiothreitol (DTT).

In particular aspects of the process, the recombinant trypsinogen comprises the amino acid sequence for porcine trypsin or bovine trypsin.

In particular aspects of the process, the solubilized recombinant trypsinogen is obtained from inclusion bodies isolated from prokaryote host cells transformed with an expression vector comprising a nucleic acid molecule encoding the recombinant trypsinogen and fermented under conditions for producing the recombinant trypsinogen.

The present invention further provides a process for preparing recombinant trypsin comprising (a) providing solubilized recombinant trypsinogen in a solubilization solution comprising a chaotropic agent, a buffer agent, and a low molecular weight reducing agent in the absence of a low molecular weight oxidizing agent at a pH at about the pI of trypsinogen or greater; (b) infusing the solubilization solution comprising the recombinant trypsinogen over time into a diluent comprising the chaotropic agent, buffer agent, and low molecular weight reducing agent in the absence of a low molecular weight oxidizing agent at a pH of about the pI of trypsinogen to provide a refold solution comprising the recombinant trypsinogen at a concentration greater than 1 g/L and less than 12.5 g/L, or of about 1.8 g/L; (c) incubating the refold solution comprising the recombinant trypsinogen for a time sufficient for the recombinant trypsinogen to refold into a conformation characteristic of native trypsinogen and form the disulfide bonds characteristic of native trypsinogen; and (d) diluting the refold solution and incubating the diluted refold solution for a time sufficient for the recombinant trypsinogen therein to auto-catalyze to provide the recombinant trypsin (i.e., activation to trypsin). In particular embodiments, the refold is in step (c) is performed at a temperature of about 10° to 12° C. In particular embodiments, activation to trypsin in step (d) is performed at a temperature of about 2° to 8° C.

In a further embodiment of the process, the recombinant trypsin is subjected to a chromatography step to provide a recombinant trypsin substantially free of tryptic peptides from the auto-catalysis of the recombinant trypsinogen and other residuals such as DNA, host cell proteins, and endotoxin. In particular aspects, the chromatography is affinity chromatography, which may be performed on a matrix comprising benzamidine, for example, a matrix comprising benzamidine.

In further embodiments of the process, the recombinant trypsin substantially free of peptides from the auto-catalysis is concentrated to provide a composition comprising the recombinant trypsin at a concentration of about 20 to 80 mg/mL.

In particular embodiments of the process, the chaotropic agent in the solubilization solution is about 5 to 10 M or about 6.45 M. In particular aspects, the chaotropic agent in the refold solution is about 1.4 to 1.8 M. In particular aspects of the present invention, the chaotropic agent in the solubilization solution and the refold solution is urea.

In particular embodiments of the process, the solubilization solution comprises 10 to 20 g/L of trypsinogen and the low molecular weight reducing agent in the solubilization solution comprising the recombinant trypsinogen is at a concentration sufficient to provide about 1 to 15 or 5 to 10

SH residues of the low molecular weight reducing agent per cysteine residue of the recombinant trypsinogen. In particular embodiments of the process, solubilization solution comprises about 16 g/L of trypsinogen and the low molecular weight reducing agent in the solubilization solution comprising the recombinant trypsinogen is at a concentration sufficient to provide about 5.7 SH residues of the low molecular weight reducing agent per cysteine residue of the recombinant trypsinogen.

In particular aspects of the process, the low molecular weight reducing agent in the refold solution comprising the recombinant trypsinogen is at a concentration sufficient to provide about 1 to 30 SH residues of the low molecular weight reducing agent per cysteine residue of the recombinant trypsinogen. In particular aspects of the process, the low molecular weight reducing agent in the refold solution comprising the recombinant trypsinogen is at a concentration sufficient to provide about 2 to about 25 SH residues of the low molecular weight reducing agent per cysteine residue of the recombinant trypsinogen. In particular aspects, the low molecular weight reducing agent in the refold solution comprising the recombinant trypsinogen is at a concentration sufficient to provide about 11 to about 23 SH residues of the low molecular weight reducing agent per cysteine residue of the recombinant trypsinogen. In particular aspects, the low molecular weight reducing agent is cysteine or cysteine hydrochloride or L-cysteine or L-cysteine hydrochloride. In particular aspects, the low molecular weight reducing agent is dithiothreitol (DTT).

In particular embodiments of the process, the buffer agent is ethanolamine. In particular aspects of the process, the recombinant trypsinogen comprises the amino acid sequence for porcine trypsin or bovine trypsin.

In particular aspects of the process, the solubilized recombinant trypsinogen is obtained from inclusion bodies isolated from prokaryote host cells transformed with an expression vector comprising a nucleic acid molecule encoding the recombinant trypsinogen and fermented under conditions for producing the recombinant trypsinogen. In particular aspects, the prokaryote host cell is *E. coli*.

The present invention further provides a process for preparing recombinant trypsin comprising (a) incubating transformed prokaryote host cells with a nucleic acid molecule encoding a trypsinogen in a suitable culture medium for a time sufficient for cell growth and the simultaneous or subsequent expression of the nucleic acid molecule encoding the trypsinogen for the formation of inclusion bodies comprising the typsinogen; (b) isolating the inclusion bodies comprising the recombinant trypsinogen from the transformed host cells; (c) solubilizing the inclusion bodies comprising the recombinant trypsinogen in a solubilization solution comprising a chaotropic agent, a buffer agent, and a low molecular weight reducing agent in the absence of a low molecular weight oxidizing agent; (d) infusing the solubilization solution comprising the recombinant trypsinogen over time into a diluent comprising the chaotropic agent, buffer agent, and low molecular weight reducing agent in the absence of a low molecular weight oxidizing agent to provide a refold solution comprising the recombinant trypsinogen at a concentration greater than 1 g/L or from about 1.6 to 1.9 g/L or of about 1.8 g/L; (e) incubating the refold solution comprising the recombinant trypsinogen for a time sufficient for the recombinant trypsinogen to refold into a conformation characteristic of native trypsinogen and form the disulfide bonds characteristic of native trypsinogen; and (f) diluting the refold solution and incubating the diluted refold solution for a time sufficient for the recombinant trypsinogen therein to auto-catalyze to provide the recombinant trypsin.

In a further embodiment of the process, the recombinant trypsin is subjected to a chromatography step to provide a recombinant trypsin substantially free of tryptic peptides from the auto-catalysis of the recombinant trypsinogen. In particular aspects, the chromatography is affinity chromatography, which may be performed on a matrix comprising benzamidine, for example, a matrix comprising benzamidine.

In further embodiments of the process, the recombinant trypsin substantially free of peptides from the auto-catalysis is concentrated to provide a composition comprising the recombinant trypsin at a concentration of about 20 to 80 mg/mL.

In particular embodiments of the process, the chaotropic agent in the solubilization solution is about 5 to 10 M or about 6.45 M. In particular aspects, the chaotropic agent in the refold solution is about 1.4 to 1.8 M. In particular aspects of the present invention, the chaotropic agent in the solubilization solution and the refold solution is urea.

In particular embodiments of the process, the solubilization solution comprises 10 to 20 g/L of trypsinogen and the low molecular weight reducing agent in the solubilization solution comprising the recombinant trypsinogen is at a concentration sufficient to provide about 1 to 15 or 5 to 10 SH residues of the low molecular weight reducing agent per cysteine residue of the recombinant trypsinogen. In particular embodiments of the process, solubilization solution comprises about 16 g/L of trypsinogen and the low molecular weight reducing agent in the solubilization solution comprising the recombinant trypsinogen is at a concentration sufficient to provide about 5.7 SH residues of the low molecular weight reducing agent per cysteine residue of the recombinant trypsinogen.

In particular aspects of the process, the low molecular weight reducing agent in the refold solution comprising the recombinant trypsinogen is at a concentration sufficient to provide about 1 to 30 SH residues of the low molecular weight reducing agent per cysteine residue of the recombinant trypsinogen. In particular aspects of the process, the low molecular weight reducing agent in the refold solution comprising the recombinant trypsinogen is at a concentration sufficient to provide about 2 to about 25 SH residues of the low molecular weight reducing agent per cysteine residue of the recombinant trypsinogen. In particular aspects, the low molecular weight reducing agent in the refold solution comprising the recombinant trypsinogen is at a concentration sufficient to provide about 11 to about 23 SH residues of the low molecular weight reducing agent per cysteine residue of the recombinant trypsinogen. In particular aspects, the low molecular weight reducing agent is cysteine or cysteine hydrochloride or L-cysteine or L-cysteine hydrochloride. In particular aspects, the low molecular weight reducing agent is dithiothreitol (DTT).

In particular embodiments of the process, the buffer agent is ethanolamine. In particular aspects of the process, the recombinant trypsinogen comprises the amino acid sequence for porcine trypsin or bovine trypsin.

In particular aspects of the process, the solubilized recombinant trypsinogen is obtained from inclusion bodies isolated from prokaryote host cells transformed with an expression vector comprising a nucleic acid molecule encoding the recombinant trypsinogen and fermented under conditions for producing the recombinant trypsinogen. In particular aspects, the prokaryote host cell is *E. coli*.

The present invention further provides a process for preparing recombinant trypsin comprising (a) providing solubilized recombinant trypsinogen in a solubilization solution comprising a chaotropic agent, a buffer agent, and a first low molecular weight reducing agent in the absence of a low molecular weight oxidizing agent at a pH of about the pI of trypsinogen or greater; (b) infusing the solubilization solution comprising the recombinant trypsinogen into a diluent comprising the chaotropic agent, buffer agent, and a second low molecular weight reducing agent in the absence of a low molecular weight oxidizing agent at a pH of about the pI of trypsinogen to provide a refold solution comprising the recombinant trypsinogen at a concentration greater than 1 g/L and less than 12.5 g/L, or from about 1.6 to 1.9 g/L or about 1.8 g/L; (c) incubating the refold solution comprising the recombinant trypsinogen for a time sufficient for the recombinant trypsinogen to refold into a conformation characteristic of native trypsinogen and form the disulfide bonds characteristic of native trypsinogen; and (d) diluting the refold solution and incubating the diluted refold mixture for a time sufficient for the recombinant trypsinogen therein to auto-catalyze to provide the recombinant trypsin.

In a further embodiment of the process, the recombinant trypsin is subjected to a chromatography step to provide a recombinant trypsin substantially free of tryptic peptides from the auto-catalysis of the recombinant trypsinogen. In particular aspects, the chromatography is affinity chromatography, for example, chromatography on a matrix comprising benzamidine.

In further embodiments of the process, the recombinant trypsin substantially free of peptides from the auto-catalysis is concentrated to provide a composition comprising the recombinant trypsin at a concentration of about 20 to 80 mg/mL.

In particular embodiments of the process, the chaotropic agent in the solubilization solution is about 5 to 10 M or about 6.45 M. In particular aspects, the chaotropic agent in the refold solution is about 1.4 to 1.8 M. In particular aspects of the present invention, the chaotropic agent in the solubilization solution and the refold solution is urea.

In particular embodiments of the process, the first low molecular weight reducing agent in the solubilization solution comprising the recombinant trypsinogen is at a concentration sufficient to provide about 1 to 15 or 5 to 10 SH residues of the low molecular weight reducing agent per cysteine residue of the recombinant trypsinogen.

In particular aspects of the process, the first and second low molecular weight reducing agent in the refold solution comprising the recombinant trypsinogen is at a concentration sufficient to provide about 1 to 30, 2 to 25, or 11 to 23 SH residues of the low molecular weight reducing agent per cysteine residue of the recombinant trypsinogen.

In particular aspects, the first low molecular weight reducing agent is dithiothreitol (DTT) and the second low molecular weight reducing agent is cysteine or cysteine hydrochloride or L-cysteine or L-cysteine hydrochloride.

In particular embodiments of the process, the buffer agent is ethanolamine. In particular aspects of the process, the recombinant trypsinogen comprises the amino acid sequence for bovine trypsin.

In particular aspects of the process, the solubilized recombinant trypsinogen is obtained from inclusion bodies isolated from prokaryote host cells transformed with an expression vector comprising a nucleic acid molecule encoding the recombinant trypsinogen and fermented under conditions for producing the recombinant trypsinogen. In particular aspects, the prokaryote host cell is *E. coli*.

Definitions

As used herein, the term "trypsin" refers to any polypeptide or protein that is capable of cleaving peptide chains mainly at the carboxyl side of the amino acids lysine or arginine, except when either is followed by proline. Protease Lys-C cleaves on the carboxyl side of lysine but not arginine. Polypeptides having such enzymatic activity have Enzyme Commission designation EC 3.4.21.4. Thus, the term includes the various isoforms of trypsin, including but not limited to, cationic trypsin or trypsin-1, anionic trypsin or trypsin-2, and mesotryspsinogen or trypsin-3. The term also includes β-trypsin and α-trypsin.

As used herein, the term "trypsinogen" refers to the zymogen form of the trypsin. A zymogen (or proenzyme) is an inactive enzyme precursor. A zymogen requires a biochemical change (such as a hydrolysis reaction revealing the active site, or changing the configuration to reveal the active site) for it to become an active enzyme.

As used herein, the term, "heterologous expression" means that the protein is experimentally put into a cell that does not normally make (i.e., express) that protein.

Heterologous polypeptide or heterologous protein thus refers to the fact that the transferred DNA coding for a polypeptide or protein such as trypsinogen was initially cloned from or derived from a different cell type or a different species from the recipient. For example, the gene encoding trypsinogen can be made synthetically and then transferred into the host organism, which as native organism does not produce that polypeptide or protein. Therefore, the genetic material encoding for the polypeptide or protein can be added to the recipient cell by recombinant cloning techniques. The genetic material that is transferred for the heterologous expression should be within a format that encourages the recipient cell to express the recombinant DNA as open reading frame (ORF) to synthesize a protein, i.e., it is put in an expression vector.

As used herein, the term, "polypeptide" refers to a molecule comprising a linear chain of amino acids or a molecule comprising two or more linear chains of amino acids covalently linked by one or more disulfide linkages.

As used herein, the term "protein" refers to a polypeptide, which has the ability to form into a specific conformation. In the context of the present invention, the terms polypeptide and protein may be used interchangeably for polypeptides of a specific length or conformation.

As used herein, the term "recombinant DNA" refers to the form of artificial DNA such as a synthetic DNA or cDNA, e.g. coding for trypsinogen that is created through the introduction of the DNA into an organism such as *E. coli* for the purpose of expression of the polypeptide or protein encoded by the recombinant DNA.

As used herein, the term "recombinant protein" thus is a protein that is derived from the recombinant DNA by expression of the recombinant DNA in the host cell.

As used herein, the term "correctly folded" protein (synonymously: "native protein" or "protein in its native conformation") such as native trypsinogen or native trypsin refers to a molecule, which has the three dimensional conformation and disulfide bridges as found in the naturally occurring, biologically active protein.

BRIEF DESCRIPTION OF THE DRAWINGS

FIG. 1 shows the amino acid sequence for porcine trypsinogen (SEQ ID NO:1) with indication of the proper disulfide bonds and the methionylated trypsinogen shown. The formula for porcine recombinant trypsin is $C_{1020}H_{1597}N_{287}O_{321}S_{14}$.

DETAILED DESCRIPTION OF THE INVENTION

The present invention provides a process for making recombinant trypsin from its zymogen trypsinogen produced from a prokaryote host cell at high yield. The process allows for refolding to take place at much higher protein concentrations than has been previously reported and in the presence of a low molecular weight reducing agent without a low molecular weight oxidizing agent, i.e., without a low molecular weight redox pair. In the art, it is typical for the refold process to be performed with a pair of reduced and oxidized low molecular weight thiol reagents (e.g., See WO2012104099). However, when performing the process disclosed herein much higher refold efficiencies may be obtained than have been previously attainable for trypsin produced from a prokaryote host cell. The ability to achieve high refold efficiencies enables the production of a recombinant trypsin at commercially relevant amounts. Recombinant trypsin is preferred for use in the production of therapeutic products over animal derived trypsin currently in use, particularly with respect to safety (absence of transmissible spongiform encephalopathies and other infectious agents) and lot-to-lot consistency.

In a typical process for preparing the recombinant trypsin according to the present invention, a prokaryotic host cell is transformed with a nucleic acid molecule, which encodes the recombinant trypsinogen, to provide a recombinant host cell. The recombinant trypsinogen may be an inactive trypsin precursor (zymogen), including derivatives or homologues of trypsinogen or any trypsin precursor that can be processed into an enzymatically active trypsin product. The amino acid sequence of the encoded recombinant trypsinogen may be that for a mammalian trypsinogen, e.g., the amino acid sequence may be that for the human, bovine, porcine, ovine, or rat trypsinogen.

For the expression of the recombinant trypsinogen, the nucleic acid molecule encoding the recombinant trypsinogen is incorporated by standard cloning techniques into an expression vector suitable for expressing the recombinant tryspsinogen in the host cell. The expression vector provides all elements necessary for expression of trypsinogen in the host cell. Suitable expression vectors are commercially available and include standard expression vectors for expression in *E. coli* such as pQET7 available from Qiagen in which the gene encoding the recombinant trypsinogen is expressed under control of the T7 promoter. Transformation of prokaryote host cells such as *E. coli* are well known in the art, for example, see Sambrook et al., Cold Spring Harbor Laboratory Press, Cold Spring Harbor, N.Y., 1998.

The recombinant prokaryote host cell is cultivated under conditions that allow for growth of the recombinant prokaryote host cell to provide a multiplicity of the recombinant host cell and expression of the recombinant nucleic acid molecule encoding the recombinant trypsinogen by formation of inclusion bodies. The recombinant prokaryotic host cell is typically cultivated in a medium suitable for growth of the host cell. Suitable liquid media for growing the host organism include synthetic media, full or half media. Media for cultivation of *E. coli* include Luria Broth (LB), 2×YT or, a fully synthetic medium based on a phosphate buffer, a nitrogen source like ammonium chloride, a carbon- and energy source like glucose or glycerol, trace elements, and an amino acid supplement to enhance growth (Korz et al., J. Biotech. 39: 59 (1994)).

After sufficient growth of the recombinant prokaryotic host cell, the cells are usually harvested, e.g. by filtration or centrifugation, and then disrupted to further isolate the recombinant trypsinogen from the broken cells. Disruption may be achieved by high pressure homogenization. Other methods for disrupting the host cells include enzymatic treatment with lysozyme and/or sonication. In a prokaryotic host such as *E. coli*, the recombinant trypsinogen is usually present in the form of insoluble inclusion bodies. The inclusion bodies may be isolated or separated from the cellular debris by centrifugation.

The isolated inclusion bodies are then solubilized to obtain the recombinant trypsinogen contained within the inclusion bodies. Solubilization of the inclusion bodies may be achieved by solubilizing the inclusion bodies in a solubilization solution comprising a chaotrophic agent, a buffer agent, and a low molecular weight reducing agent in the absence of a low molecular weight oxidizing agent. The solubilization solution does not comprise a redox pair comprising a low molecular weight reducing agent and a low molecular weight oxidizing agent. The pH of the solubilization solution is generally at a pH that is about the same as or greater than the pI for the trypsinogen. In general, concentration of inclusion bodies is such that the trypsinogen is at a high concentration, in particular a concentration of about 5 to 18 g/L, or 10 to 15 g/L, or about 15 g/L. The low molecular weight reducing agent is at a concentration that sufficient to provide about 1 to 15 or about 5 to 10 SH residues of the low molecular weight reducing agent per cysteine residue of the trypsinogen. The inclusion bodies are incubated at a temperature and a time sufficient to effect the solubilization of substantially all of the recombinant trypsinogen to provide solubilized recombinant trypsinogen. For example, the incubation may be for 20 to 180 minutes, or between 30 and 120 minutes, or between 45 and 90 minutes. Typically, incubation is performed under mild shaking or mixing.

In a particular embodiment, the chaotropic agent is urea, which may be used at a concentration from about 6 to 8.5 M, or about 6.45 M. In particular embodiments, the buffer agent may be ethanolamine, which may be at a concentration from 50 to 200 mM, or about 180 mM. In particular embodiments, the low molecular weight reducing agent may be cysteine at a concentration of about 50 mM.

In particular embodiments, the low molecular reducing agent in the solubilization solution is cysteine. In particular embodiments, the low molecular weight reducing agent in the solubilization solution is dithiothreitol (DTT).

The solubilized recombinant trypsinogen is not in the conformation or tertiary structure characteristic of native trypsinogen and does not have the disulfide bonds characteristic for native trypsinogen. Therefore, the solubilized recombinant trypsinogen is subjected to a refold process wherein the solubilized trypsinogen is allowed to refold into the conformation or tertiary structure characteristic of native insulin and form the disulfide bonds characteristic for native trypsin.

Following solubilzation, the solubilization solution comprising the solubilized recombinant trypsinogen is diluted over time to provide a refold solution comprising the solubilized recombinant trypsinogen at a concentration of about 1 g/L to about 5 g/L or about 1.8 g/L, the chaotropic agent at a concentration that is about 20 to 30% or about 22% of its concentration in the solubilization solution, and the low molecular weight reducing agent at a concentration sufficient to provide about 1 to 30 or about 2 to 25 or about 11 to 23 SH residues of the low molecular reducing agent per cysteine residue of the recombinant trypsinogen. In particular embodiments, the low molecular weight reducing agent at a concentration sufficient to provide about 10 to 30 SH residues of the low molecular reducing agent per cysteine residue of the recombinant trypsinogen. The refold solution does not include a low molecular weight oxidizing agent to provide a redox pair comprising the low molecular weight reducing agent and a low molecular weight oxidizing agent. The pH of the refold solution is at about the pI of the trypsinogen, about 8.5 to 9.0. The refold solution is incubated at a time and temperature suitable for refolding of the solubilized trypsinogen into its native conformation or tertiary structure, i.e., a conformation characteristic of native trypsin and which has formed the disulfide bonds characteristic of native trypsinogen. In particular embodiments, the incubation is at about 10 to 12° C. and the time is about 15 hours.

In particular embodiments, the solubilization solution comprising the solubilized recombinant trypsinogen is infused into a diluent solution comprising the chaotropic agent, buffer agent, and low molecular weight reducing agent without a low molecular weight oxidizing agent at a concentration such that over time of the infusion to provide the refold solution comprising the solubilized recombinant trypsinogen at a concentration of about 1 g/L to about 5 g/L or about 1.8 g/L, the chaotropic agent at a concentration that is about 20 to 30% of its concentration in the solubilization solution, and the low molecular weight reducing agent at a concentration sufficient to provide about 1 to 15 SH residues of the low molecular reducing agent per cysteine residue of the recombinant trypsinogen. The volume of diluent solution is about 6 to 8 or about 7.34 volumes of the dilute per volume of solubilization solution. The rate of infusion may be constant and may be over a time period of about eight to 15 hours. While the infusion rate is dependent upon the total time of the infusion, the rate is constant throughout a given infusion.

In particular embodiments, the low molecular reducing agent in the refold solution is cysteine. In particular embodiments, the low molecular weight reducing agent in the refold solution is dithiothreitol (DTT). In particular embodiments, the low molecular weight reducing agent in the refold solution is a combination of cysteine and DTT. For example, the DTT and the cysteine may be at a concentration sufficient to provide about 1 to 30 SH residues per cysteine residue of the trypsinogen. In a particular embodiment, the concentration provides about 2 SH residues per cysteine residue of the trypsinogen.

In particular embodiments, the diluent may further comprise a calcium salt, e.g., calcium chloride, and/or an amino acid, e.g., arginine. Thus in particular embodiments, the refold solution comprises the solubilized recombinant trypsinogen at a concentration of about 1 g/L to about 5 g/L or about 1.8 g/L, the chaotropic agent at a concentration that is about 20 to 30% or about 22% of its concentration in the solubilization solution, the low molecular weight reducing agent at a concentration sufficient to provide about 1 to 30, 2 to 25, or 11 to 23SH residues of the low molecular reducing agent per cysteine residue of the recombinant trypsinogen, an amino acid such as arginine, and a calcium salt such as calcium chloride.

In a particular aspect, the solubilized recombinant trypsinogen is infused into a diluent solution comprising about 0.7 M urea, about 540 mM arginine, about 11 mM calcium chloride, and about 6 mM L-cysteine hydrochloride, and about 50 mM diluent buffer agent (e.g., Tris-HCl) at about pH 8.5 over about 8 to 15 hours to provide a refold solution. The final composition of the refold solution is about 1.8 g recombinant trypsinogen/L in about 22 mM of the buffer agent, about 44 mM Tris, about 1.4 to 1.8 M urea, about 11.3 mM low molecular weight reducing agent, about 0 to 1000 mM or about 475 mM arginine and about 9.7 mM calcium chloride. The pH for the refold solution may be about 8.5 to 9.0. Refolding is carried out at about 10 to 12° C. for a time sufficient for a substantial amount of the recombinant trypsinogen to refold into the conformation similar to that of native trypsinogen, which in particular embodiments may be about 15 hours.

The refold solution may further contain agents to prevent self-activation of trypsinogen. Such an inhibitor can be, i.e. benzamidine, which is typically used in a concentration of about 1 to 100 mM, or about 5 to 10 mM.

The inventors have discovered that refolding trypsinogen comprising the amino acid sequence of porcine trypsin may be achieved in an embodiment wherein the low molecular weight reducing agent in the solubilization solution is at a concentration that provides about 1 to 15 or 5 to 10 SH residues per cysteine residue of the trypsinogen and the refold solution provides about 1 to 30 or 2 to 25 or 11 to 23 SH residues per cysteine residue of the trypsinogen.

The inventors have discovered that refolding trypsinogen comprising the amino acid sequence of bovine trypsin may be achieved in an embodiment wherein the low molecular weight reducing agent in the solubilization solution is at a concentration that provides about 2 to 3 SH residues per cysteine residue of the trypsinogen and the refold solution provides about 2 SH residues per cysteine residue of the trypsinogen. For example, the solubilization solution may comprise DTT and the refold solution may comprise a combination of cysteine and DTT. For example, the solubilization solution may comprise DTT at a concentration sufficient to provide about 2 to 3 SH residues per cysteine residue of the trypsinogen and the refold solution may comprise a mixture of DTT and cysteine at a concentration sufficient to provide about 2 SH residues per cysteine residue of the trypsinogen in the refold solution.

Processing of converting or activating the recombinant trypsinogen into recombinant trypsin is generally achieved by autocatalytic cleavage of the recombinant trypsinogen into recombinant trypsin or by incubation of trypsinogen with the protease enterokinase. Suitable conditions for autocatalytic cleavage of trypsinogen to trypsin are known in the art (see for example, Kay and Kassell, J. Biol. Chem. 216: 6661 (1971)). Suitable conditions for proteolytic digestion of trypsinogen with enterokinase are given, e.g. in Grant and Hermon-Taylor, Biochem. J. 147: 363 (1975). A suitable process for autocatlysis is as follows.

The refolded recombinant trypsinogen is concentrated about 10-fold by tangential flow filtration (TFF) and then diafiltered against three volumes of diafiltration buffer containing a buffer agent and a chaotropic agent, for example, 50 mM Tris, 2.5 M urea, pH 8.0. The filtration may be carried out at room temperature. The concentrated recombinant trypsinogen is diluted three-fold with diluent buffer comprising a buffer agent and a calcium salt, for example, about 50 mM Tris, 75 mM calcium chloride, pH 8.0, which may be chilled to about 2-8° C. prior to use to provide primarily recombinant trypsin in the β-form, to provide a cleavage buffer. A chilled cleavage buffer provides the recombinant trypsin in primarily the β-trypsin form whereas cleavage buffer at room temperature increases the amount of α-trypsin. After addition of the diluent, the cleavage buffer is incubated for a time and temperature sufficient for the production of the recombinant trypsin. Under chilled conditions, primarily recombinant β-trypsin is produced. The diluted trypsinogen undergoes auto-catalysis (activation) to produce trypsin via removal of the short leader sequence noted in FIG. 1. For example, the cleavage may be carried out at a chilled temperature 2-8° C. for 9-13 hours (optimally 11 hours) without mixing.

In a particular embodiments, the cleavage solution has a pH of about 7 to 9, or 7.5 to 8.5 and calcium chloride at a concentration of between 10 and 100 mM, or about 50 mM. The solution is then typically incubated at about 2 to 37° C., or 20 to 37° C., or 2° to 8° C. until the recombinant trypsinogen is completely converted to trypsin as described by Kay and Kassell, J. Biol. Chem. 216: 6661 (1971). Conducting activation at 2° to 8° C. reduces impurities due to auto-catalysis of trypsin.

Following conversion or activation of the recombinant trypsinogen into recombinant trypsin, the recombinant trypsin is separated from process and product related impurities such as tryptic peptides that arise during the autocatalytic step.

The recombinant trypsin may be clarified via centrifugation and/or 0.2μ filtration. In general, to the recombinant trypsin is added sufficient sodium chloride to produce a final concentration of about 50-500 mM sodium chloride, or about 50 mM sodium chloride. Following mixing and adjustment of the pH to 8.0, the material is clarified by 0.2μ filtration.

Benzamidine (BA) chromatography is performed to reduce tryptic peptides that arise via auto-catalysis of the trypsin, as well as other process and product related impurities. For example, BA Sepharose 4 Fast Flow (high sub) column may be used. The clarified, activated trypsin is loaded at a target of 30 g of recombinant trypsin per L of resin onto a BA column (tested range 9-30 g/L). Loading, washing and elution of the column may be performed at a target residence time of 5 minutes. The column is equilibrated in about 50 mM Tris, 50 mM CaCl$_2$ and 50 mM NaCl, pH 8.0. After loading, the column is first washed with 50 mM Tris, 50 mM CaCl$_2$, and 50 mM NaCl, pH 8.0, followed by a second wash of 50 mM CaCl$_2$ and 50 mM NaCl. The product is eluted with 10 mM HCl, 50 mM CaCl$_2$ and 50 mM NaCl into a buffer heel of 10 mM HCl and 50 mM CaCl$_2$. The heel volume is approximately five times the column volume. The recombinant trypsin product is collected in a single BA pool based on UV absorbance.

The BA pool is transferred to a TFF system and concentrated by ultrafiltration (5 kD molecular weight cut-off membrane) to a protein concentration as determined by absorbance at 280 mm of between 20 and 80 mg/mL, or 40 to 80 mg/mL or 60 to 80 mg/mL. The concentrated BA pool is then diafiltered against 10 mM HCl for a minimum of 5 diavolumes. The concentrated recombinant trypsin is aliquoted and stored at −20° C. or lower.

The process disclosed herein may be used to provide trypsin of any origin. For example, process may be used to produce recombinant porcine trypsin (SEQ ID NO:6) from recombinant porcine trypsinogen (SEQ ID NO:1), recombinant bovine trypsin (SEQ ID NO:7) from recombinant bovine trypsinogen (SEQ ID NO:2), recombinant human trypsin (SEQ ID NO:8) from recombinant human trypsinogen (SEQ ID NO:3), recombinant rat trypsin (SEQ ID NO:9) from recombinant rat trypsinogen (SEQ ID NO:4), and a recombinant Ser172Ala porcine trypsin (SEQ ID NO:10) from recombinant Ser172Ala trypsinogen (SEQ ID NO:5).

The recombinant trypsin product resulting from the above-described process may be used for various biotechnological applications. For example, trypsin is commonly used in biological research during proteomics experiments to digest proteins into peptides for mass spectrometry analysis, e.g. in-gel digestion. Trypsin is particularly suited for this, since it has a very well defined specificity, as it hydrolyzes only the peptide bonds in which the carbonyl group is contributed either by an Arginine or Lysine residue.

Trypsin is also used to process fusion proteins. Often, fusion proteins contain a tag such as an affinity tag, e.g. a His-tag, to purify and/or identify the fusion protein and the protein part of interest. Engineering a proteolytic cleavage site between the tag and the rest of the fusion protein allows trypsin to cleave and remove the tag to further characterize the protein of interest.

The trypsin product may also be used for processing of proteins for use in vaccines.

The trypsin product may also be used for processing of an insulin precursor such as proinsulin, preferably human proinsulin, in a process for manufacturing insulin, preferably recombinant insulin. In this process, the insulin C-peptide or any other peptide located between the A- and B-chains of insulin is cleaved off by action of trypsin.

The trypsin product may also be used to remove adherent cells from growth surfaces (plates or bottles).

Moreover, trypsin in its microbial form can also be used to dissolve blood clots and treat inflammation in its pancreatic form. Trypsin is further used to pre-digest baby food. It can break down the protein molecules to assist the child's digestion as its stomach is not strong enough to digest bigger protein molecules.

The following examples are intended to promote a further understanding of the present invention.

Example 1

This example describes the preparation of a recombinant porcine trypsin product comprising primarily β-trypsin. The amino acid sequence for porcine trypsin is shown in SEQ ID NO:1.

Preparation of Fermentor Inoculum 1.1 L of inoculum media (yeast extract, sodium chloride, and glycerol) is sterilized into each of five 4-liter flasks. The flasks are pre-incubated at 37° C. and then kanamycin sulfate solution is added to a final concentration of 42.5 μg/mL in each flask. The flasks are inoculated with recombinant *E. coli* that are capable of expressing recombinant trypsinogen and the inoculated flasks are incubated at 37° C. at 200 rpm on a shaker.

Optical density at 600 nm is monitored during cultivation until an optical density of 1.5 to 3.0 is attained at which time the five flasks are pooled and then transferred to a production fermentor.

Fermentation in Batch, then Fed-Batch Mode

The fermentation is performed in a 1400 L working volume fermentation vessel. The production medium consists of 2% yeast extract, 0.43% glycerol, phosphate, magnesium, antifoam, citric acid and trace elements batched in the 2000 L fermentor. Kanamycin sulfate is added to the medium to maintain selective pressure. The culture is grown at 32° C., pH 7.0 (automatic ammonium hydroxide addition), dissolved oxygen at 10% saturation and fermentor back pressure of 8 psi.

A feed stream of yeast extract and glycerol is initiated at 3 hours post inoculation using a feed rate that increases in multiple steps. Dissolved oxygen concentration is maintained at or above 10% of saturation. Antifoam solution is added on an as-needed basis. Isopropyl β-D-1 thiogalactopyranoside (IPTG) is added to a concentration of 0.4 mM when the culture reaches an $OD_{600}$ of 60 to induce expression. The fermentation is terminated 4 hours post-induction and the culture is cooled to 15° C. or less. When the production fermentor temperature falls below 15° C. the cool down is complete and cell harvest may begin.

Harvest and Capture

When the culture is 15° C. or less, the cells are harvested by continuous centrifugation using a disc stack centrifuge. The concentrated whole cells are re-suspended in Tris/EDTA buffer.

The re-suspended whole cells are chilled to 15° C. or less and lysed by multiple passes through a high pressure homogenizer. The lysed cells release inclusion bodies (IBs) which are collected by centrifugation. The inclusion bodies are washed by dilution with Tris/EDTA buffer, and are then collected by centrifugation. Six liters of inclusion body slurry is aliquoted per bag and stored at −70° C. pending further processing.

Solubilization of Inclusion Bodies

The solubilization of inclusion bodies is performed at a starting target of 12.5 g of trypsinogen per liter. Inclusion bodies are thawed at ambient temperature and solubilized in an ethanolamine (182 mM), urea (6.45 M) and L-cysteine hydrochloride (50 mM) buffer at 20° C. with mixing. The target pH for the solubilization is and more preferably 9.5 to 10.5.

Refold

The solubilized trypsinogen is infused at a constant rate into about 7.34 or more volumes of diluent comprising 50 mM Tris, 0.7 M urea, 540 mM arginine, 11 mM calcium chloride, 6 mM L-cysteine hydrochloride, pH 8.5 over 8 to 15 hours to provide a refold solution comprising 1.5 g trypsinogen/L in 22 mM ethanolamine, 44 mM Tris, 1.4 M urea (range 1.4 to 1.8 M), 11.3 mM cysteine hydrochloride, 475 mM arginine (range 0 to 1000 mM) and 9.7 mM calcium chloride. The inventors have found that the arginine in addition to its role in promoting refolding, also inhibits pre-mature activation of the trypsinogen. The prevention of pre-mature activation allows for tighter control over the activation process and decreases the auto-catalytic degradation of the trypsin. The pH for the refold is typically at about 8.5 to 9.0. While the infusion rate is dependent upon the total time of the infusion, the rate is constant throughout a given infusion. Refolding is carried out at about 10 to 12° C. for and more preferably for 15 hours.

Conversion of Trypsinogen to Trypsin

Using a tangential flow filtration (TFF) membrane with a nominal molecular weight cut-off of 8 kD, the refolded trypsinogen is concentrated 10-fold and then diafiltered against three volumes of 50 mM Tris, 2.5 M urea, pH 8.0. The filtration is carried out at room temperature. Prior to use, the TFF membrane is flushed with 100 L of the water for injection (WFI) per $m^2$ of membrane area and then equilibrated with 5 L of diafiltration buffer per $m^2$ of membrane area. The 2.5 M urea concentration is used to inhibit pre-mature activation of the trypsinogen. The prevention of pre-mature activation allows for tighter control over the activation process and decreases the auto-catalytic degradation of the trypsin.

The concentrated trypsinogen is diluted three-fold with 50 mM Tris, 75 mM calcium chloride, pH 8.0 optimally chilled to 2-8° C. prior to use. Buffer at room temperature was also tested but found to increase the levels of α-trypsin (for some purposes considered an impurity). After addition of the diluent, the mixture is stirred for approximately 10 minutes.

The diluted trypsinogen undergoes auto-catalysis (activation) to produce trypsin via removal of the short leader sequence noted in FIG. 1. This process is carried out at 2-8° C. for 9-13 hours (optimally 11 hours) without mixing.

Exogenously added trypsin is widely used in the art to initiate activation of trypsinogen; however, as shown herein tryspsinogen which is essentially inactive, particularly at a urea concentration of 2.5 M, does contain sufficient activity to initiate activation following dilution of the concentrated trypsinogen. Thus, the process disclosed herein, which relies on the activity of trypsinogen to initiate activation, is simpler and more amenable to commercial manufacture.

Purification and Preparation of Chromatography Load

The activated trypsin is clarified via centrifugation and/or 0.2μ filtration. To the clarified trypsin is added sufficient sodium chloride to produce a final concentration of 50-500 mM, preferentially 50 mM. Following mixing and adjustment of pH to 8.0, the material is clarified by 0.2μ filtration.

Example 2

This example provides benzamidine (BA) chromatography to reduce tryptic peptides that arise via auto-catalysis of the trypsin, as well as other process and product related impurities.

BA chromatography is performed on a Benzamidine Sepharose 4 Fast Flow (high sub) column.

The clarified, activated trypsin from Example 1 is loaded at a target of 30 g of β-trypsin per liter of resin onto a BA column (tested range 9-30 g/L). Loading, washing and elution of the column are performed at a target residence time of 5 minutes. The column is equilibrated in 50 mM Tris, 50 mM $CaCl_2$ and 50 mM NaCl, pH 8.0. After loading, the column is first washed with 50 mM Tris, 50 mM $CaCl_2$ and 50 mM NaCl, pH 8.0, followed by a second wash of 50 mM $CaCl_2$ and 50 mM NaCl. The product is eluted with 10 mM HCl, 50 mM $CaCl_2$ and 50 mM NaCl into a buffer heel of 10 mM HCl and 50 mM $CaCl_2$. The heel volume is approximately five times the column volume. The product is collected in a single pool based on UV absorbance.

Preparation and Storage of Concentrated Recombinant Trypsin

The BA Pool is transferred to a TFF system and concentrated by ultrafiltration (5 kD molecular weight cut-off membrane) to a protein concentration as determined by absorbance at 280 mm of between 20 and 80 mg/mL, preferably to 40 to 80 mg/mL and most preferably to 60 to 80 mg/mL. The concentrated BA Pool is then diafiltered against 10 mM HCl for a minimum of 7 diavolumes. The trypsin produced was able to cleave the artificial substrate tosyl-arginine methyl ester as well as detach cultured mammalian cell from growth surfaces. The concentrated recombinant trypsin is aliquoted and stored at −70° C.

Yields

The refold yield with the process is approximately 60%. This compares very well to the 20% or less reported in the literature. The yield through the entire process from inclusion body solubilization to concentrated recombinant trypsin is approximately 45%.

Example 3

A prophetic example in which recombinant bovine trypsin product comprising primarily β-trypsin may be performed as follows. The amino acid sequence for bovine trypsin is shown in SEQ ID NO:2.

Preparation of Fermentor Inoculum 1.1 L of inoculum media (yeast extract, sodium chloride, and glycerol) is sterilized into each of five 4-liter flasks. The flasks are pre-incubated at 37° C. and then kanamycin sulfate solution is added to a final concentration of 42.5 μg/mL in each flask. The flasks are inoculated with recombinant E. coli that are capable of expressing recombinant trypsinogen and the inoculated flasks are incubated at 37° C. at 200 rpm on a shaker.

Optical density at 600 nm is monitored during cultivation until an optical density of 1.5 to 3.0 is attained at which time the five flasks are pooled and then transferred to a production fermentor.

Fermentation in Batch, then Fed-Batch Mode

The fermentation is performed in a 2000 L total volume fermentation vessel. The production medium consists of 2% yeast extract, 0.43% glycerol, phosphate, magnesium, antifoam, citric acid and trace elements batched in the 2000 L fermentor. Kanamycin sulfate is added to the medium to maintain selective pressure. The culture is grown at 32° C., pH 7.0 (automatic ammonium hydroxide addition), dissolved oxygen at 10% saturation and fermentor back pressure of 8 psi.

A feed stream of yeast extract and glycerol is initiated at 3 hours post inoculation using a feed rate that increases in multiple steps. Dissolved oxygen concentration is maintained at or above 10% of saturation. Antifoam solution is added on an as-needed basis. Isopropyl β-D-1 thiogalactopyranoside (IPTG) is added to a concentration of 0.4 mM when the culture reaches an $OD_{600}$ of 60 to induce expression. The fermentation is terminated 4 hours post-induction and the culture is cooled to 15° C. or less. When the production fermentor temperature falls below 15° C. the cool down is complete and cell harvest may begin.

Harvest and Capture

When the culture is 15° C. or less, the cells are harvested by continuous centrifugation using a disc stack centrifuge. The concentrated whole cells are re-suspended in Tris/EDTA buffer.

The re-suspended whole cells are chilled to 15° C. or less and lysed by multiple passes through a high pressure homogenizer. The lysed cells release inclusion bodies (IBs) which are collected by centrifugation. The inclusion bodies are washed by dilution with Tris/EDTA buffer, and are then collected by centrifugation. Six liters of inclusion body slurry is aliquoted per bag and stored at −70° C. pending further processing.

Solubilization of Inclusion Bodies

The solubilization of inclusion bodies is performed at a starting target of 12.5 g of trypsinogen per liter. Inclusion bodies are thawed at ambient temperature and solubilized in an ethanolamine (182 mM), urea (6.45 M) and dithiothreitol (DTT) (5 mM) buffer at 20° C. with mixing. The target pH for the solubilization is and more preferably 9.5 to 10.5.

Refold

The solubilized trypsinogen is infused at a constant rate into about 7.34 volumes of diluent comprising 50 mM Tris, 0.7 M urea, 540 mM arginine, 11 mM calcium chloride, 284 to 586 μM L-cysteine hydrochloride, pH 8.5 over 8 to 15 hours to provide a refold solution comprising 1.5 g trypsinogen/L in 22 mM ethanolamine, 44 mM Tris, 1.4 M urea (range 1.4 to 1.8 M), 600 μM DTT, 250 to 500 μM cysteine hydrochloride, 475 mM arginine (range 0 to 1000 mM) and 9.7 mM calcium chloride. The pH for the refold is typically at about 8.5 to 9.0. While the infusion rate is dependent upon the total time of the infusion, the rate is constant throughout a given infusion. Refolding is carried out at about 10 to 12° C. for and more preferably for 15 hours.

Conversion of Trypsinogen to Trypsin

Using a tangential flow filtration (TFF) membrane with a nominal molecular weight cut-off of 8 kD, the refolded trypsinogen is concentrated 10-fold and then diafiltered against three volumes of 50 mM Tris, 2.5 M urea, pH 8.0. The filtration is carried out at room temperature. Prior to use, the TFF membrane is flushed with 100 L of the water for injection (WFI) per $m^2$ of membrane area and then equilibrated with 5 L of diafiltration buffer per $m^2$ of membrane area.

The concentrated trypsinogen is diluted three-fold with 50 mM Tris, 75 mM calcium chloride, pH 8.0 optimally chilled to 2-8° C. prior to use. Buffer at room temperature was also tested but found to increase the levels of α-trypsin (for some purposes considered an impurity). After addition of the diluent, the mixture is stirred for approximately 10 minutes.

The diluted trypsinogen undergoes auto-catalysis (activation) to produce trypsin via removal of the short leader sequence noted in FIG. 1. This process is carried out at 2-8° C. for 9-13 hours (optimally 11 hours) without mixing.

Purification and Preparation of Chromatography Load

The activated trypsin is clarified via centrifugation and/or 0.2μ filtration. To the clarified trypsin is added sufficient sodium chloride to produce a final concentration of 50-500 mM, preferentially 50 mM. Following mixing and adjustment of pH to 8.0, the material is clarified by 0.2μ filtration.

TABLE OF SEQUENCES

| SEQ ID NO. | DESCRIPTION | SEQUENCE |
|---|---|---|
| 1 | Sus scrufa (Porcine) trypsinogen Cleavage site between 9 and 10 | MFPTDDDDKIVGGYTCAANSIPYQVSLNSGSHF CGGSLINSQWVVSAAHCYKSRIQVRLGEHNIDVL EGNEQFINAAKIITHPNFNGNTLDNDIMLIKLSSP ATLNSRVATVSLPRSCAAAGTECLISGWGNTKSS GSSYPSLLQCLKAPVLSDSSCKSSYPGQITGNMIC VGFLEGGKDSCQGDSGGPVVCNGQLQGIVSWGY GCAQKNKPGVYTKVCNYVNWIQQTIAAN |
| 2 | Bos taurus (Bovine) trypsinogen Cleavage site between 23 and 24 | MHPLLILAFVGAAVAFPSDDDDKIVGGYTCAE NSVPYQVSLNAGYHFCGGSLINDQWVVSAAHCY QYHIQVRLGEYNIDVLEGGEQFIDASKIIRHPKYS SWTLDNDILLIKLSTPAVINARVSTLALPSACASG STECLISGWGNTLSSGVNYPDLLQCLEAPLLSHA DCEASYPGEITNNMICAGFLEGGKDSCQGDSGGP VACNGQLQGIVSWGYGCAQKGKPGVYTKVCNY VDWIQETIAANS |

TABLE OF SEQUENCES

| SEQ ID NO. | DESCRIPTION | SEQUENCE |
|---|---|---|
| 3 | Homo sapiens (Human) trypsinogen Cleavage site between 23 and 24 | MNLLLILTFVAAAVAAPFDDDDKIVGGYICEEN SVPYQVSLNSGYHFCGGSLISEQWVVSAGHCYK SRIQVRLGEHNIEVLEGNEQFINAAKIIRHPKYNS RTLDNDILLIKLSSPAVINSRVSAISLPTAPPAAGT ESLISGWGNTLSSGADYPDELQCLDAPVLSQAEC EASYPGKITNNMFCVGFLEGGKDSCQGDSGGPV VSNGELQGIVSWGYGCAQKNRPGVYTKVYNYV DWIKDTIAANS |
| 4 | Rattus norvegicus (Rat) trypsinogen Cleavage site between 24 and 25 | MKALIFLAFLGAAVALPLDDDDDKIVGGYTCQ KNSLPYQVSLNAGYHFCGGSLINSQWVVSAAHC YKSRIQVRLGEHNIDVVEGGEQFIDAAKIIRHPSY NANTFDNDIMLIKLNSPATLNSRVSTVSLPRSCGS SGTKCLVSGWGNTLSSGTNYPSLLQCLDAPVLSD SSCKSSYPGKITSNMFCLGFLEGGKDSCQGDSGG PVVCNGQLQGVVSWGYGCAQKGKPGVYTKVC NYVNWIQQTVAAN |
| 5 | Artificial Sequence Modified porcine trypsinogen comprising Ala at position 172 | MFPTDDDDKIVGGYTCAANSIPYQVSLNSGSHF CGGSLINSQWVVSAAHCYKSRIQVRLGEHNIDVL EGNEQFINAAKIITHPNFNGNTLDNDIMLIKLSSP ATLNSRVATVSLPRSCAAAGTECLISGWGNTKSS GSSYPSLLQCLKAPVLSDSSCKSSYPGQITGNMIC VGFLEGGKDACQGDSGGPVVCNGQLQGIVSWG YGCAQKNKPGVYTKVCNYVNWIQQTIAAN |
| 6 | Sus scrufa (Porcine) trypsin | IVGGYTCAANSIPYQVSLNSGSHFCGGSLINSQW VVSAAHCYKSRIQVRLGEHNIDVLEGNEQFINAA KIITHPNFNGNTLDNDIMLIKLSSPATLNSRVATV SLPRSCAAAGTECLISGWGNTKSSGSSYPSLLQCL KAPVLSDSSCKSSYPGQITGNMICVGFLEGGKDS CQGDSGGPVVCNGQLQGIVSWGYGCAQKNKPG VYTKVCNYVNWIQQTIAAN |
| 7 | Bos taurus (Bovine) trypsin | IVGGYTCAENSVPYQVSLNAGYHFCGGSLINDQ WVVSAAHCYQYHIQVRLGEYNIDVLEGGEQFID ASKIIRHPKYSSWTLDNDILLIKLSTPAVINARVST LALPSACASGSTECLISGWGNTLSSGVNYPDLLQ CLEAPLLSHADCEASYPGEITNNMICAGFLEGGK DSCQGDSGGPVACNGQLQGIVSWGYGCAQKGK PGVYTKVCNYVDWIQETIAANS |
| 8 | Homo sapiens (Human) trypsin | IVGGYICEENSVPYQVSLNSGYHFCGGSLISEQW VVSAGHCYKSRIQVRLGEHNIEVLEGNEQFINAA KIIRHPKYNSRTLDNDILLIKLSSPAVINSRVSAISL PTAPPAAGTESLISGWGNTLSSGADYPDELQCLD APVLSQAECEASYPGKITNNMFCVGFLEGGKDSC QGDSGGPVVSNGELQGIVSWGYGCAQKNRPGV YTKVYNYVDWIKDTIAANS |
| 9 | Rattus norvegicus (Rat) trypsin | IVGGYTCQKNSLPYQVSLNAGYHFCGGSLINSQ WVVSAAHCYKSRIQVRLGEHNIDVVEGGEQFID AAKIIRHPSYNANTFDNDIMLIKLNSPATLNSRVS TVSLPRSCGSSGTKCLVSGWGNTLSSGTNYPSLL QCLDAPVLSDSSCKSSYPGKITSNMFCLGFLEGG KDSCQGDSGGPVVCNGQLQGVVSWGYGCAQKG KPGVYTKVCNYVNWIQQTVAAN |
| 10 | Artificial Sequence Modified porcine trypsin comprising Ala at position 172 | IVGGYTCAANSIPYQVSLNSGSHFCGGSLINSQW VVSAAHCYKSRIQVRLGEHNIDVLEGNEQFINAA KIITHPNFNGNTLDNDIMLIKLSSPATLNSRVATV SLPRSCAAAGTECLISGWGNTKSSGSSYPSLLQCL KAPVLSDSSCKSSYPGQITGNMICVGFLEGGKDA CQGDSGGPVVCNGQLQGIVSWGYGCAQKNKPG VYTKVCNYVNWIQQTIAAN |

While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is limited only by the claims attached herein.

---

What is claimed:

1. A process for refolding recombinant trypsinogen produced from a prokaryote host cell comprising:

(a) providing the recombinant trypsinogen at a concentration of from 5 to 15 g/L in a solubilization solution comprising a chaotropic agent, a first buffer agent, and a first low molecular weight reducing agent, wherein the solubilization solution does not include a low molecular weight oxidizing agent that would provide a redox pair with the first low molecular weight reducing agent; and (b) infusing the solubilization solution comprising the recombinant trypsinogen of step (a) over time into a diluent comprising a second buffer agent, a second low molecular weight reducing agent, the chaotropic agent, and arginine to provide a refold solution that comprises the recombinant trypsinogen at a concentration greater than 1 g/L, the chaotropic agent at from 20% to 30% of its concentration in the solubilization solution of step (a), the first and second buffer agents, arginine, and the first and second low molecular weight reducing agents and incubating the refold solution for a time sufficient for the recombinant trypsinogen to refold into a conformation characteristic of native trypsinogen and form the disulfide bonds characteristic of native trypsinogen, wherein the refold solution does not include a low molecular weight oxidizing agent that would provide a redox pair with either the first or second low molecular weight reducing agents.

2. The process of claim 1, wherein in both steps (a) and (b) the chaotropic agent is urea.

3. The process of claim 1, wherein the chaotropic agent is in the refold solution at a concentration of from 1.4 to 1.8 M.

4. The process of claim 1, wherein the first and second low molecular weight reducing agents are cysteine or cysteine hydrochloride.

5. The process of claim 1, wherein the first low molecular weight reducing agent is in the solubilization solution at a concentration sufficient to provide from 1 to 15 SH residues of the first low molecular weight reducing agent per cysteine residue of the recombinant trypsinogen.

6. The process of claim 1, wherein the first and second low molecular weight reducing agents are in the refold solution at a concentration sufficient to provide from 1 to 30 SH residues of the low molecular weight reducing agents per cysteine residue of the recombinant trypsinogen.

7. The process of claim 1, further comprising:
(c) diluting the refold solution and incubating the diluted refold solution for a time sufficient for the recombinant trypsinogen therein to auto-catalyze to provide the recombinant trypsin.

8. The process of claim 7, wherein the recombinant trypsin is subjected to a chromatography step to provide a recombinant trypsin substantially free of tryptic peptides from the auto-catalysis of the recombinant trypsinogen and host cell residuals, including DNA, host cell proteins and endotoxin.

9. The process of claim 8, wherein the recombinant trypsin substantially free of peptides from the auto-catalysis is concentrated to provide a composition comprising the recombinant trypsin at a concentration of from 20 to 80 mg/mL.

10. The process of claim 8, wherein the chromatography step comprises affinity chromatography.

11. The process of claim 10, wherein the affinity chromatography is performed on a matrix comprising benzamidine.

12. The process of claim 11, wherein the affinity chromatography is performed on a matrix comprising benzamidine-Sepharose.

13. The process of claim 7, wherein the first buffer agent is ethanolamine.

14. The process of claim 7, wherein in both steps (a) and (b) the chaotropic agent is urea.

15. The process of claim 7, wherein the chaotropic agent is in the refold solution at a concentration of from 1.4 to 1.8 M.

16. The process of claim 7, wherein the first and second reducing agents are cysteine or cysteine hydrochloride.

17. The process of claim 7, wherein the first low molecular weight reducing agent is in the solubilization solution at a concentration sufficient to provide from 1 to 15 SH residues of the first low molecular weight reducing agent per cysteine residue of the recombinant trypsinogen.

18. The process of claim 7, wherein the first and second low molecular weight reducing agents are in the refold solution at a concentration sufficient to provide from 1 to 30 SH residues of the low molecular weight reducing agents per cysteine residue of the recombinant trypsinogen.

19. The process of claim 1, wherein the recombinant trypsinogen is obtained from inclusion bodies isolated from the prokaryote host cells.

20. The process of claim 1, wherein the first buffer agent is ethanolamine.

21. The process of claim 1, wherein the second buffer agent is Tris.

* * * * *

SEQUENCE LISTING

<160> NUMBER OF SEQ ID NOS: 10

<210> SEQ ID NO 1
<211> LENGTH: 232
<212> TYPE: PRT
<213> ORGANISM: Sus scrufa

<400> SEQUENCE: 1

Met Phe Pro Thr Asp Asp Asp Lys Ile Val Gly Gly Tyr Thr Cys
1               5                   10                  15

Ala Ala Asn Ser Ile Pro Tyr Gln Val Ser Leu Asn Ser Gly Ser His
                20                  25                  30

Phe Cys Gly Gly Ser Leu Ile Asn Ser Gln Trp Val Val Ser Ala Ala
            35                  40                  45

His Cys Tyr Lys Ser Arg Ile Gln Val Arg Leu Gly Glu His Asn Ile
        50                  55                  60

Asp Val Leu Glu Gly Asn Glu Gln Phe Ile Asn Ala Ala Lys Ile Ile
65                  70                  75                  80

Thr His Pro Asn Phe Asn Gly Asn Thr Leu Asp Asn Asp Ile Met Leu
                85                  90                  95

Ile Lys Leu Ser Ser Pro Ala Thr Leu Asn Ser Arg Val Ala Thr Val
                100                 105                 110

Ser Leu Pro Arg Ser Cys Ala Ala Ala Gly Thr Glu Cys Leu Ile Ser
            115                 120                 125

Gly Trp Gly Asn Thr Lys Ser Ser Gly Ser Ser Tyr Pro Ser Leu Leu
        130                 135                 140

Gln Cys Leu Lys Ala Pro Val Leu Ser Asp Ser Ser Cys Lys Ser Ser
145                 150                 155                 160

Tyr Pro Gly Gln Ile Thr Gly Asn Met Ile Cys Val Gly Phe Leu Glu
                165                 170                 175

Gly Gly Lys Asp Ser Cys Gln Gly Asp Ser Gly Gly Pro Val Val Cys
            180                 185                 190

Asn Gly Gln Leu Gln Gly Ile Val Ser Trp Gly Tyr Gly Cys Ala Gln
        195                 200                 205

Lys Asn Lys Pro Gly Val Tyr Thr Lys Val Cys Asn Tyr Val Asn Trp
        210                 215                 220

Ile Gln Gln Thr Ile Ala Ala Asn
225                 230

<210> SEQ ID NO 2
<211> LENGTH: 247
<212> TYPE: PRT
<213> ORGANISM: Bos taurus

<400> SEQUENCE: 2

Met His Pro Leu Leu Ile Leu Ala Phe Val Gly Ala Ala Val Ala Phe
1               5                   10                  15

Pro Ser Asp Asp Asp Asp Lys Ile Val Gly Gly Tyr Thr Cys Ala Glu
                20                  25                  30

Asn Ser Val Pro Tyr Gln Val Ser Leu Asn Ala Gly Tyr His Phe Cys

```
            35                  40                  45
Gly Gly Ser Leu Ile Asn Asp Gln Trp Val Ser Ala Ala His Cys
    50                  55                  60
Tyr Gln Tyr His Ile Gln Val Arg Leu Gly Glu Tyr Asn Ile Asp Val
65                  70                  75                  80
Leu Glu Gly Gly Glu Gln Phe Ile Asp Ala Ser Lys Ile Ile Arg His
                85                  90                  95
Pro Lys Tyr Ser Ser Trp Thr Leu Asp Asn Asp Ile Leu Leu Ile Lys
            100                 105                 110
Leu Ser Thr Pro Ala Val Ile Asn Ala Arg Val Ser Thr Leu Ala Leu
        115                 120                 125
Pro Ser Ala Cys Ala Ser Gly Ser Thr Glu Cys Leu Ile Ser Gly Trp
    130                 135                 140
Gly Asn Thr Leu Ser Ser Gly Val Asn Tyr Pro Asp Leu Leu Gln Cys
145                 150                 155                 160
Leu Glu Ala Pro Leu Leu Ser His Ala Asp Cys Glu Ala Ser Tyr Pro
                165                 170                 175
Gly Glu Ile Thr Asn Asn Met Ile Cys Ala Gly Phe Leu Glu Gly Gly
            180                 185                 190
Lys Asp Ser Cys Gln Gly Asp Ser Gly Gly Pro Val Ala Cys Asn Gly
        195                 200                 205
Gln Leu Gln Gly Ile Val Ser Trp Gly Tyr Gly Cys Ala Gln Lys Gly
    210                 215                 220
Lys Pro Gly Val Tyr Thr Lys Val Cys Asn Tyr Val Asp Trp Ile Gln
225                 230                 235                 240
Glu Thr Ile Ala Ala Asn Ser
                245

<210> SEQ ID NO 3
<211> LENGTH: 247
<212> TYPE: PRT
<213> ORGANISM: Homo sapiens

<400> SEQUENCE: 3

Met Asn Leu Leu Leu Ile Leu Thr Phe Val Ala Ala Val Ala Ala
1               5                   10                  15
Pro Phe Asp Asp Asp Asp Lys Ile Val Gly Gly Tyr Ile Cys Glu Glu
                20                  25                  30
Asn Ser Val Pro Tyr Gln Val Ser Leu Asn Ser Gly Tyr His Phe Cys
            35                  40                  45
Gly Gly Ser Leu Ile Ser Glu Gln Trp Val Val Ser Ala Gly His Cys
    50                  55                  60
Tyr Lys Ser Arg Ile Gln Val Arg Leu Gly Glu His Asn Ile Glu Val
65                  70                  75                  80
Leu Glu Gly Asn Glu Gln Phe Ile Asn Ala Ala Lys Ile Ile Arg His
                85                  90                  95
Pro Lys Tyr Asn Ser Arg Thr Leu Asp Asn Asp Ile Leu Leu Ile Lys
            100                 105                 110
Leu Ser Ser Pro Ala Val Ile Asn Ser Arg Val Ser Ala Ile Ser Leu
        115                 120                 125
Pro Thr Ala Pro Pro Ala Ala Gly Thr Glu Ser Leu Ile Ser Gly Trp
    130                 135                 140
Gly Asn Thr Leu Ser Ser Gly Ala Asp Tyr Pro Asp Glu Leu Gln Cys
145                 150                 155                 160
```

Leu Asp Ala Pro Val Leu Ser Gln Ala Glu Cys Glu Ala Ser Tyr Pro
                165                 170                 175

Gly Lys Ile Thr Asn Asn Met Phe Cys Val Gly Phe Leu Glu Gly Gly
            180                 185                 190

Lys Asp Ser Cys Gln Gly Asp Ser Gly Gly Pro Val Val Ser Asn Gly
        195                 200                 205

Glu Leu Gln Gly Ile Val Ser Trp Gly Tyr Gly Cys Ala Gln Lys Asn
    210                 215                 220

Arg Pro Gly Val Tyr Thr Lys Val Tyr Asn Tyr Val Asp Trp Ile Lys
225                 230                 235                 240

Asp Thr Ile Ala Ala Asn Ser
                245

<210> SEQ ID NO 4
<211> LENGTH: 247
<212> TYPE: PRT
<213> ORGANISM: Rattus norvegicus

<400> SEQUENCE: 4

Met Lys Ala Leu Ile Phe Leu Ala Phe Leu Gly Ala Ala Val Ala Leu
1               5                   10                  15

Pro Leu Asp Asp Asp Asp Lys Ile Val Gly Gly Tyr Thr Cys Gln
            20                  25                  30

Lys Asn Ser Leu Pro Tyr Gln Val Ser Leu Asn Ala Gly Tyr His Phe
        35                  40                  45

Cys Gly Gly Ser Leu Ile Asn Ser Gln Trp Val Val Ser Ala Ala His
    50                  55                  60

Cys Tyr Lys Ser Arg Ile Gln Val Arg Leu Gly Glu His Asn Ile Asp
65                  70                  75                  80

Val Val Glu Gly Gly Glu Gln Phe Ile Asp Ala Ala Lys Ile Ile Arg
                85                  90                  95

His Pro Ser Tyr Asn Ala Asn Thr Phe Asp Asn Asp Ile Met Leu Ile
            100                 105                 110

Lys Leu Asn Ser Pro Ala Thr Leu Asn Ser Arg Val Ser Thr Val Ser
        115                 120                 125

Leu Pro Arg Ser Cys Gly Ser Ser Gly Thr Lys Cys Leu Val Ser Gly
    130                 135                 140

Trp Gly Asn Thr Leu Ser Ser Gly Thr Asn Tyr Pro Ser Leu Leu Gln
145                 150                 155                 160

Cys Leu Asp Ala Pro Val Leu Ser Asp Ser Ser Cys Lys Ser Ser Tyr
                165                 170                 175

Pro Gly Lys Ile Thr Ser Asn Met Phe Cys Leu Gly Phe Leu Glu Gly
            180                 185                 190

Gly Lys Asp Ser Cys Gln Gly Asp Ser Gly Gly Pro Val Val Cys Asn
        195                 200                 205

Gly Gln Leu Gln Gly Val Val Ser Trp Gly Tyr Gly Cys Ala Gln Lys
    210                 215                 220

Gly Lys Pro Gly Val Tyr Thr Lys Val Cys Asn Tyr Val Asn Trp Ile
225                 230                 235                 240

Gln Gln Thr Val Ala Ala Asn
                245

<210> SEQ ID NO 5
<211> LENGTH: 232
<212> TYPE: PRT
<213> ORGANISM: Artificial sequence

```
<220> FEATURE:
<223> OTHER INFORMATION: Porcine trypsinogen comprising Ala at position
      172

<400> SEQUENCE: 5

Met Phe Pro Thr Asp Asp Asp Lys Ile Val Gly Gly Tyr Thr Cys
1               5                   10                  15

Ala Ala Asn Ser Ile Pro Tyr Gln Val Ser Leu Asn Ser Gly Ser His
                20                  25                  30

Phe Cys Gly Gly Ser Leu Ile Asn Ser Gln Trp Val Val Ser Ala Ala
                35                  40                  45

His Cys Tyr Lys Ser Arg Ile Gln Val Arg Leu Gly Glu His Asn Ile
    50                  55                  60

Asp Val Leu Glu Gly Asn Glu Gln Phe Ile Asn Ala Ala Lys Ile Ile
65                  70                  75                  80

Thr His Pro Asn Phe Asn Gly Asn Thr Leu Asp Asn Asp Ile Met Leu
                85                  90                  95

Ile Lys Leu Ser Ser Pro Ala Thr Leu Asn Ser Arg Val Ala Thr Val
                100                 105                 110

Ser Leu Pro Arg Ser Cys Ala Ala Ala Gly Thr Glu Cys Leu Ile Ser
                115                 120                 125

Gly Trp Gly Asn Thr Lys Ser Ser Gly Ser Ser Tyr Pro Ser Leu Leu
    130                 135                 140

Gln Cys Leu Lys Ala Pro Val Leu Ser Asp Ser Ser Cys Lys Ser Ser
145                 150                 155                 160

Tyr Pro Gly Gln Ile Thr Gly Asn Met Ile Cys Val Gly Phe Leu Glu
                165                 170                 175

Gly Gly Lys Asp Ala Cys Gln Gly Asp Ser Gly Gly Pro Val Val Cys
                180                 185                 190

Asn Gly Gln Leu Gln Gly Ile Val Ser Trp Gly Tyr Gly Cys Ala Gln
    195                 200                 205

Lys Asn Lys Pro Gly Val Tyr Thr Lys Val Cys Asn Tyr Val Asn Trp
                210                 215                 220

Ile Gln Gln Thr Ile Ala Ala Asn
225                 230

<210> SEQ ID NO 6
<211> LENGTH: 223
<212> TYPE: PRT
<213> ORGANISM: Sus scrufa

<400> SEQUENCE: 6

Ile Val Gly Gly Tyr Thr Cys Ala Ala Asn Ser Ile Pro Tyr Gln Val
1               5                   10                  15

Ser Leu Asn Ser Gly Ser His Phe Cys Gly Gly Ser Leu Ile Asn Ser
                20                  25                  30

Gln Trp Val Val Ser Ala Ala His Cys Tyr Lys Ser Arg Ile Gln Val
                35                  40                  45

Arg Leu Gly Glu His Asn Ile Asp Val Leu Glu Gly Asn Glu Gln Phe
    50                  55                  60

Ile Asn Ala Ala Lys Ile Ile Thr His Pro Asn Phe Asn Gly Asn Thr
65                  70                  75                  80

Leu Asp Asn Asp Ile Met Leu Ile Lys Leu Ser Ser Pro Ala Thr Leu
                85                  90                  95

Asn Ser Arg Val Ala Thr Val Ser Leu Pro Arg Ser Cys Ala Ala Ala
                100                 105                 110
```

```
Gly Thr Glu Cys Leu Ile Ser Gly Trp Gly Asn Thr Lys Ser Ser Gly
            115                 120                 125

Ser Ser Tyr Pro Ser Leu Leu Gln Cys Leu Lys Ala Pro Val Leu Ser
        130                 135                 140

Asp Ser Ser Cys Lys Ser Ser Tyr Pro Gly Gln Ile Thr Gly Asn Met
145                 150                 155                 160

Ile Cys Val Gly Phe Leu Glu Gly Gly Lys Asp Ser Cys Gln Gly Asp
                165                 170                 175

Ser Gly Gly Pro Val Val Cys Asn Gly Gln Leu Gln Gly Ile Val Ser
                180                 185                 190

Trp Gly Tyr Gly Cys Ala Gln Lys Asn Lys Pro Gly Val Tyr Thr Lys
            195                 200                 205

Val Cys Asn Tyr Val Asn Trp Ile Gln Gln Thr Ile Ala Ala Asn
        210                 215                 220

<210> SEQ ID NO 7
<211> LENGTH: 224
<212> TYPE: PRT
<213> ORGANISM: Bos taurus

<400> SEQUENCE: 7

Ile Val Gly Gly Tyr Thr Cys Ala Glu Asn Ser Val Pro Tyr Gln Val
1               5                   10                  15

Ser Leu Asn Ala Gly Tyr His Phe Cys Gly Gly Ser Leu Ile Asn Asp
            20                  25                  30

Gln Trp Val Val Ser Ala Ala His Cys Tyr Gln Tyr His Ile Gln Val
        35                  40                  45

Arg Leu Gly Glu Tyr Asn Ile Asp Val Leu Glu Gly Gly Glu Gln Phe
    50                  55                  60

Ile Asp Ala Ser Lys Ile Ile Arg His Pro Lys Tyr Ser Ser Trp Thr
65                  70                  75                  80

Leu Asp Asn Asp Ile Leu Leu Ile Lys Leu Ser Thr Pro Ala Val Ile
                85                  90                  95

Asn Ala Arg Val Ser Thr Leu Ala Leu Pro Ser Ala Cys Ala Ser Gly
            100                 105                 110

Ser Thr Glu Cys Leu Ile Ser Gly Trp Gly Asn Thr Leu Ser Ser Gly
        115                 120                 125

Val Asn Tyr Pro Asp Leu Leu Gln Cys Leu Glu Ala Pro Leu Leu Ser
    130                 135                 140

His Ala Asp Cys Glu Ala Ser Tyr Pro Gly Glu Ile Thr Asn Asn Met
145                 150                 155                 160

Ile Cys Ala Gly Phe Leu Glu Gly Gly Lys Asp Ser Cys Gln Gly Asp
                165                 170                 175

Ser Gly Gly Pro Val Ala Cys Asn Gly Gln Leu Gln Gly Ile Val Ser
            180                 185                 190

Trp Gly Tyr Gly Cys Ala Gln Lys Gly Lys Pro Gly Val Tyr Thr Lys
        195                 200                 205

Val Cys Asn Tyr Val Asp Trp Ile Gln Glu Thr Ile Ala Ala Asn Ser
    210                 215                 220

<210> SEQ ID NO 8
<211> LENGTH: 224
<212> TYPE: PRT
<213> ORGANISM: Homo sapiens

<400> SEQUENCE: 8
```

```
Ile Val Gly Gly Tyr Ile Cys Glu Glu Asn Ser Val Pro Tyr Gln Val
1               5                   10                  15

Ser Leu Asn Ser Gly Tyr His Phe Cys Gly Gly Ser Leu Ile Ser Glu
            20                  25                  30

Gln Trp Val Val Ser Ala Gly His Cys Tyr Lys Ser Arg Ile Gln Val
        35                  40                  45

Arg Leu Gly Glu His Asn Ile Glu Val Leu Glu Gly Asn Glu Gln Phe
    50                  55                  60

Ile Asn Ala Ala Lys Ile Ile Arg His Pro Lys Tyr Asn Ser Arg Thr
65                  70                  75                  80

Leu Asp Asn Asp Ile Leu Leu Ile Lys Leu Ser Ser Pro Ala Val Ile
                85                  90                  95

Asn Ser Arg Val Ser Ala Ile Ser Leu Pro Thr Ala Pro Pro Ala Ala
                100                 105                 110

Gly Thr Glu Ser Leu Ile Ser Gly Trp Gly Asn Thr Leu Ser Ser Gly
            115                 120                 125

Ala Asp Tyr Pro Asp Glu Leu Gln Cys Leu Asp Ala Pro Val Leu Ser
    130                 135                 140

Gln Ala Glu Cys Glu Ala Ser Tyr Pro Gly Lys Ile Thr Asn Asn Met
145                 150                 155                 160

Phe Cys Val Gly Phe Leu Glu Gly Gly Lys Asp Ser Cys Gln Gly Asp
                165                 170                 175

Ser Gly Gly Pro Val Val Ser Asn Gly Glu Leu Gln Gly Ile Val Ser
                180                 185                 190

Trp Gly Tyr Gly Cys Ala Gln Lys Asn Arg Pro Gly Val Tyr Thr Lys
            195                 200                 205

Val Tyr Asn Tyr Val Asp Trp Ile Lys Asp Thr Ile Ala Ala Asn Ser
    210                 215                 220

<210> SEQ ID NO 9
<211> LENGTH: 223
<212> TYPE: PRT
<213> ORGANISM: Rattus norvegicus

<400> SEQUENCE: 9

Ile Val Gly Gly Tyr Thr Cys Gln Lys Asn Ser Leu Pro Tyr Gln Val
1               5                   10                  15

Ser Leu Asn Ala Gly Tyr His Phe Cys Gly Gly Ser Leu Ile Asn Ser
            20                  25                  30

Gln Trp Val Val Ser Ala Ala His Cys Tyr Lys Ser Arg Ile Gln Val
        35                  40                  45

Arg Leu Gly Glu His Asn Ile Asp Val Val Glu Gly Gly Glu Gln Phe
    50                  55                  60

Ile Asp Ala Ala Lys Ile Ile Arg His Pro Ser Tyr Asn Ala Asn Thr
65                  70                  75                  80

Phe Asp Asn Asp Ile Met Leu Ile Lys Leu Asn Ser Pro Ala Thr Leu
                85                  90                  95

Asn Ser Arg Val Ser Thr Val Ser Leu Pro Arg Ser Cys Gly Ser Ser
                100                 105                 110

Gly Thr Lys Cys Leu Val Ser Gly Trp Gly Asn Thr Leu Ser Ser Gly
            115                 120                 125

Thr Asn Tyr Pro Ser Leu Leu Gln Cys Leu Asp Ala Pro Val Leu Ser
    130                 135                 140

Asp Ser Ser Cys Lys Ser Ser Tyr Pro Gly Lys Ile Thr Ser Asn Met
```

```
                145                 150                 155                 160
Phe Cys Leu Gly Phe Leu Glu Gly Gly Lys Asp Ser Cys Gln Gly Asp
                    165                 170                 175

Ser Gly Gly Pro Val Val Cys Asn Gly Gln Leu Gln Gly Val Val Ser
                180                 185                 190

Trp Gly Tyr Gly Cys Ala Gln Lys Gly Lys Pro Gly Val Tyr Thr Lys
            195                 200                 205

Val Cys Asn Tyr Val Asn Trp Ile Gln Gln Thr Val Ala Ala Asn
    210                 215                 220

<210> SEQ ID NO 10
<211> LENGTH: 223
<212> TYPE: PRT
<213> ORGANISM: Artificial sequence
<220> FEATURE:
<223> OTHER INFORMATION: Porcine trypsin comprising Ala at position 172

<400> SEQUENCE: 10

Ile Val Gly Gly Tyr Thr Cys Ala Ala Asn Ser Ile Pro Tyr Gln Val
1               5                   10                  15

Ser Leu Asn Ser Gly Ser His Phe Cys Gly Gly Ser Leu Ile Asn Ser
                20                  25                  30

Gln Trp Val Val Ser Ala Ala His Cys Tyr Lys Ser Arg Ile Gln Val
            35                  40                  45

Arg Leu Gly Glu His Asn Ile Asp Val Leu Glu Gly Asn Glu Gln Phe
        50                  55                  60

Ile Asn Ala Ala Lys Ile Ile Thr His Pro Asn Phe Asn Gly Asn Thr
65                  70                  75                  80

Leu Asp Asn Asp Ile Met Leu Ile Lys Leu Ser Ser Pro Ala Thr Leu
                85                  90                  95

Asn Ser Arg Val Ala Thr Val Ser Leu Pro Arg Ser Cys Ala Ala Ala
            100                 105                 110

Gly Thr Glu Cys Leu Ile Ser Gly Trp Gly Asn Thr Lys Ser Ser Gly
        115                 120                 125

Ser Ser Tyr Pro Ser Leu Leu Gln Cys Leu Lys Ala Pro Val Leu Ser
    130                 135                 140

Asp Ser Ser Cys Lys Ser Ser Tyr Pro Gly Gln Ile Thr Gly Asn Met
145                 150                 155                 160

Ile Cys Val Gly Phe Leu Glu Gly Gly Lys Asp Ala Cys Gln Gly Asp
                165                 170                 175

Ser Gly Gly Pro Val Val Cys Asn Gly Gln Leu Gln Gly Ile Val Ser
                180                 185                 190

Trp Gly Tyr Gly Cys Ala Gln Lys Asn Lys Pro Gly Val Tyr Thr Lys
            195                 200                 205

Val Cys Asn Tyr Val Asn Trp Ile Gln Gln Thr Ile Ala Ala Asn
    210                 215                 220
```